Jan. 1, 1952 C. G. DUEHRSEN Plant Pat. 1,062
ROSE PLANT
Filed April 27, 1950
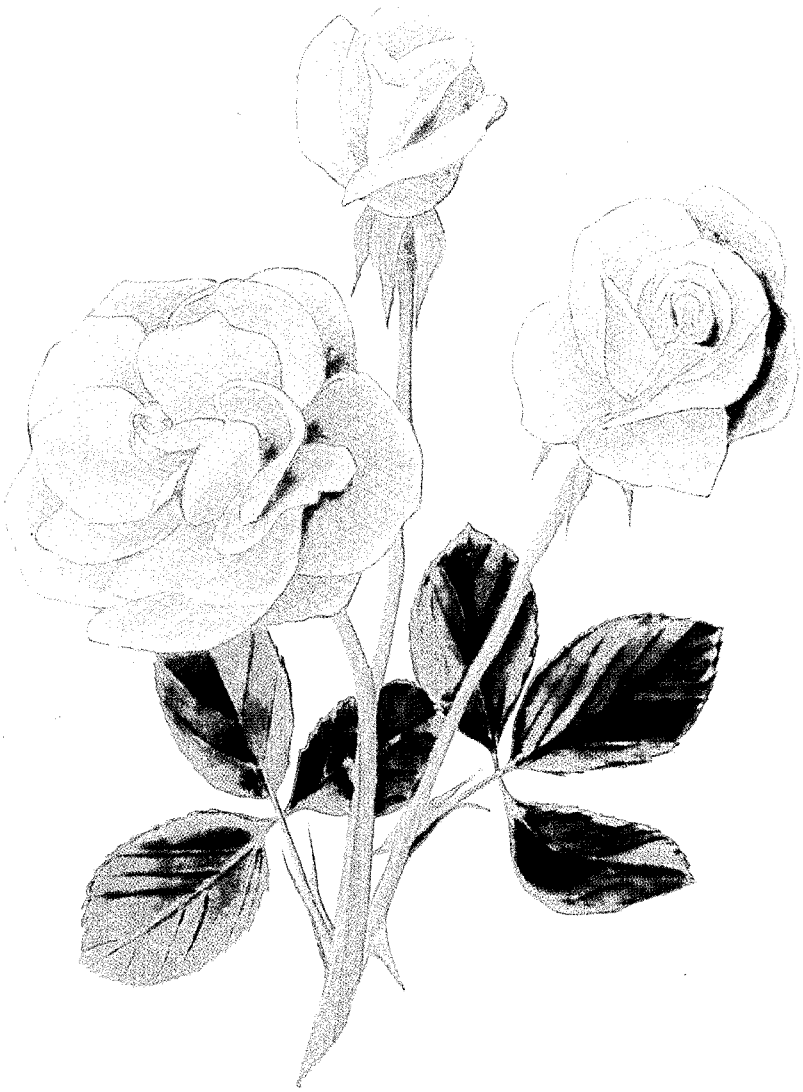
INVENTOR
Carl George Duehrsen
BY Orville M. Kile
PLANT PATENT AGENT Patented Jan. 1, 1952

Plant Pat. 1,062

UNITED STATES PATENT OFFICE 1,062

ROSE PLANT

Carl George Duehrsen, Montebello, Calif., assignor to Howard & Smith, Montebello, Calif.

Application April 27, 1950, Serial No. 158,420

1 Claim. (Cl. 47—61)

My present invention relates to a new and distinct variety of floribunda rose plant and resulted from a cross made by me in southern California between the variety Margy (unpatented) and one of my unnamed seedlings. It is in the red-flowered class although the color tends more toward scarlet than in other similar known varieties. My new variety has been asexually reproduced by budding in a nursery at Montebello, California and its characteristics appear to be permanent.

Unlike most floribundas, the flowers of my new variety appear individually on the small stems of the clusters. Each stem of the cluster ends in a terminal bud and does not develop side buds. The flowers are rather large for floribundas and are longer-lasting than is usual with this type rose.

The accompanying illustrations show three specimens of the flower of my new variety of rose in various stages of opening, together with portions of the foliage and stems. All are shown in as nearly their true colors as could be achieved by the artist.

Following is a more detailed description of my new rose variety. Color nomenclature is in accordance with Ridgway's Color Standards and Nomenclature except where the ordinary dictionary term is obviously intended.

*The plant*

Growth habit: Very strong and vigorous grower. Bush spreading and full. Attains a height of 3 to 3½ feet.

Blooming habit: Very free and floriferous bloomer with multiple buds to each stem. Flowers form in clusters but each stem of the cluster ends in a terminal bud rather than having side buds as is usual with the floribunda type plant.

Stems: Strong, light green, shining. About 2 to 3 inches long. Has a few thorns which are outward-pointing, about ¼ inch long and light green with usually a reddish overlay.

Foliage: Imparipinnate, with 5 to 7 leaflets. Average in quantity.

*Leaflets.*—Oval, average about ¾ inch wide by 1½ inches long. Texture is leathery. Color is dark green.

*Stipules.*—Prominent, with extended points.

*The flower*

Bud:

*Size.*—About 1¼ to 1½ inches long and almost as broad at its base, just before the petals begin to unfurl.

*Shape.*—Globular at this same stage, although it is pointed before calyx breaks and when tightly closed.

*Color.*—Dark velvety red just before unfurling.

*Opening.*—Slow and even.

*Peduncle.*—Sturdy; 2½ to 3 inches long.

*Calyx.*—Short and stocky.

*Sepals.*—Simple; reflex early, about 1 inch long.

Bloom:

*Size.*—Small to medium; diameter of fully opened bloom averages about 3 inches.

*Form.*—Compact and high-centered, opening into loose formation but with stamens usually covered until flower is old.

*Color.*—Dark red, tending toward scarlet. This color is not shown at all in Ridgway's Color Standards—the nearest lies between Tyrian Rose (Plate XII) and Spectrum Red (Plate I).

Petals:

*Form.*—Globular, slightly recurved. Edge entire.

*Size.*—1¼ by 1¾ inches.

*Behavior.*—Persistent.

*Color.*—Bright dark red, many with a white stripe through the center—this latter feature being found in no other red floribunda now on the market, so far as I am aware.

Petalage: Usually 20 to 25 petals.

Reproductive organs:

*Pistils.*—Medium number. Bunched in center of flower. *Styles*—prominent.

*Stamens.*—Many, surrounding styles. Five-eighths to 1 inch in length. *Filaments*—golden. *Anthers*—large and brown.

Longevity: Flower lasts much longer when cut than do other known roses of similar type.

Fragrance: Has slight tea scent.

Having thus disclosed my invention, I claim:

The new and distinct variety of floribunda rose plant, substantially as herein shown and described, characterized particularly by its free and floriferous blooming habit; its full and vigorous growth; the lack of lateral buds on the flower stems; the longevity of its flowers when cut; the dark, velvety red buds; and the rather compact form and vivid red color of the flowers with frequent appearance of a white stripe through center of petals.

CARL GEORGE DUEHRSEN.

No references cited.